United States Patent [19]

Ueda et al.

[11] Patent Number: 4,575,868

[45] Date of Patent: Mar. 11, 1986

[54] POSITRON COMPUTED TOMOGRAPH DEVICE

[75] Inventors: Ken Ueda, Oume; Kenichi Okajima, Hoya; Katsumi Takami, Tokyo, all of Japan

[73] Assignees: Agency of Industrial Science & Technology; Ministry of International Trade & Industry, both of Tokyo, Japan

[21] Appl. No.: 530,545

[22] Filed: Sep. 9, 1983

[30] Foreign Application Priority Data

Sep. 9, 1982 [JP] Japan .................................. 57-155945

[51] Int. Cl.⁴ .............................................. G01T 1/20
[52] U.S. Cl. ........................................ 378/4; 378/401; 364/414; 250/363 S
[58] Field of Search ....... 250/363 S, 363 SA, 363 SB; 364/414; 378/4–10, 19, 86

[56] References Cited

U.S. PATENT DOCUMENTS

| | | | |
|---|---|---|---|
| 4,150,292 | 4/1979 | Ter-Pogossian | 250/363 S |
| 4,259,578 | 3/1981 | Thompson | 250/363 S |
| 4,284,890 | 8/1981 | Thompson | 250/363 S |
| 4,352,018 | 9/1982 | Tanaka et al. | 378/4 |
| 4,415,807 | 11/1983 | Friauf et al. | 250/363 S |
| 4,463,263 | 7/1984 | Padawer | 250/308 |

OTHER PUBLICATIONS

S. Derenzo, et al, "Imaging Properties of a Positron Tomograph with 280 B60 Crystals", IEEE Transactions on Nuclear Science, vol. NS-28, No. 1, Feb. 1981.
N. Nohara, et al, "Positologica: A Positron ECT Device with a Continuously Rotating Detector Ring", IEEE Transactions on Nuclear Science, vol. NS-27, No. 3, Jun. 1980.
Budinger, et al, "Trends and Prospects for Circular Ring Positron Cameras", IEEE Transactions on Nuclear Science, vol. NS-26, No. 2, Apr. 1979.
S. Derenzo, et al, "The Donner 280-Crystal High Resolution Positron Tomogragh", IEEE Transactions on Nuclear Science, vol. NS-26, No. 2, Apr. 1979.

Primary Examiner—Craig E. Church
Assistant Examiner—Charles Wieland
Attorney, Agent, or Firm—Oblon, Fisher, Spivak, McClelland & Maier

[57] ABSTRACT

A positron-computed tomograph device is enabled to suppress the noise component of data for attenuation correction by continuing measurement of the relative angle between a gamma ray source for attenuation correction and detector pair out of a plurality of detectors thereby determining whether or not, at a given moment, the gamma ray source is present within the zone of measurement allocated for a specific detector pair which has detected coincidence and, when the determination ascertains that the source is not present in the aforementioned zone of measurement, avoiding measurement of coincidence or preventing data on coincidence from being stored in a memory.

7 Claims, 7 Drawing Figures

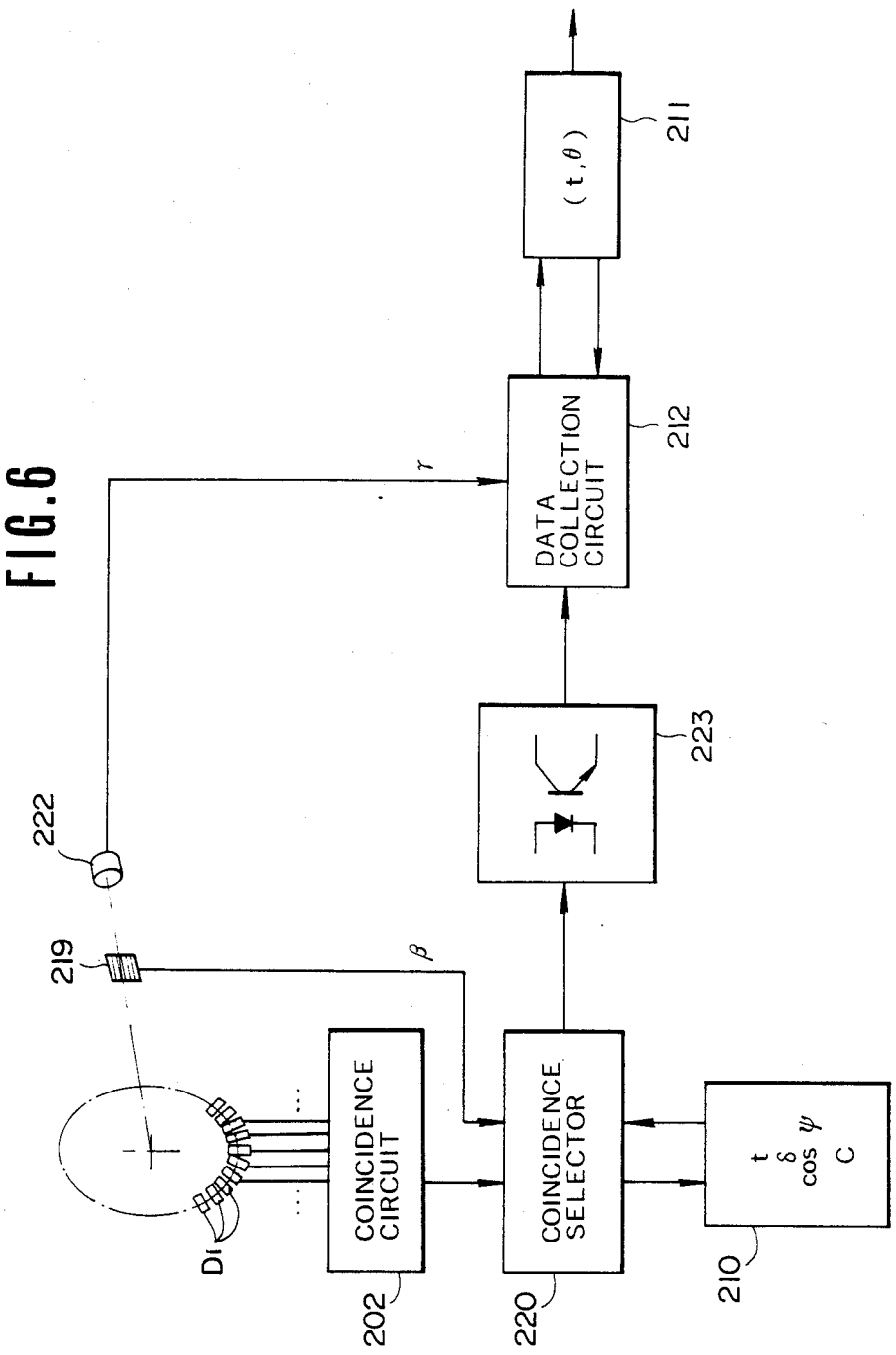

POSITRON COMPUTED TOMOGRAPH DEVICE

BACKGROUND OF THE INVENTION

1. Field of the Invention

This invention relates to a device for positron-computed tomography, and more particularly to a positron-computed tomograph device provided with a mechanism capable of suppressing the noise component contained in the attenuation correction data obtained by irradiating a given subject with gamma rays for attenuation correction.

2. Description of the Prior Art

In positron-computed tomography (PCT), which is one form of emission-computed tomography (ECT), for the purpose of obtaining a reconstructed cross-sectional image with good quantitative properties on the basis of the distribution of a radio isotope within the subject, two gamma rays (annihilation gamma rays) which are emitted in diametrically opposite directions at the time of annihilation of a positron within the subject are coincidently counted (coincidence). The data obtained by this coincidence requires attenuation correction. Several different methods have been proposed for this attenuation correction. One of these methods (N. Nohara, et al. "POSITOLOGICA: A Positron ECT Device with a Continuously Rotating Detector Ring", IEEE Transactions on Nuclear Science, Vol. NS-27, No. 3, pp. 1128-1136) entails use of a positron-computed tomograph device incorporating, as an emission source for attenuation correction, a gamma ray source formed of positron-emitting radionuclides and effects desired attenuation correction by rotating this source within a desired plane section around the subject while measuring the transmittance of annihilation gamma rays through the subject and computing the attenuation correction based on the data obtained by the measurement (hereinafter referred to as "attenuation correction data").

Even by the method of attenuation correction described above, since the absorption of gamma rays by the subject is still heavy, there is an inevitable disadvantage that the measured coincidence rate obtainable with the emission source of the intensity generally available for attenuation correction falls short of reaching the desired level.

Consequently, either allowance of an ample time for the measurement for the purpose of suppressing the statistical noise present in the data or the use of data including heavy statistical noise in the subsequent processing is inevitable.

To be more specific, as is generally known, the measured coincidence will always include a noise component due to accidental coincidence and scattered coincidence in addition to the true coincidence (coincidence in the form of signals). The rate of true coincidence increases in direct proportion to the intensity of the emission source for attenuation correction under the conditions which render the dead time of the circuit negligible. By contrast, the rate of accidental coincidence increases in direct proportion to the square of the intensity of the emission source. Thus, the ratio of signal to noise in the measured data is degraded in proportion as the radioactive intensity of the emission source increases. By measuring the accidental coincidence by the method of delayed coincidence and subtracting the result of this measurement, therefore, the measured data may be freed from the deviation due to the noise. When this method of correction is carried out, however, the statistical noise in the data tends to increase. For this reason, it is unwise to increase excessively the intensity of the emission source for attenuation correction and it is difficult to obtain transmittance data of a low noise level in a short length of time.

As a measure to lower the rate of accidental coincidence, one might consider disposing lead shields one each at the opposite sides of the emission source for attenuation correction which is revolved around the space intervening between the subject and a plurality of scintillation detectors circumferentially spaced around the subject so as to minimize the effect of the emission source exerted upon the detectors other than those falling in the direction of measurement. Even by this method, the accidental coincidence is inevitably measured among the detectors. Thus, the suppression of noise by this method has its limit.

In the circumstance, development of a PCT device which is capable of suppressing the noise component of the data for attenuation correction, enhancing the resolvability, and producing a reconstructed image of excellent quality has been desired. Further, development of a technique which enables a mechanism capable of performing such advantageous attenuation correction to be adapted for various devices such as, for example, a device utilizing a wobbling scanner, a device for straight-rotary composite scanning (C. W. Williams, et al: IEEE, Vol. NS-28, No. 2, pp. 1736-1740, 1981), a device utilizing a dichotomic scanner (Z. H. Cho, et al: IEEE, Vol. NS-28, No. 1, pp. 94-98, 1981), and a device utilizing non-scanning (S. E. Derenzo, et al: IEEE, Vol. NS-28, No. 1, pp. 81-89, 1981) has been in demand.

SUMMARY OF THE INVENTION

The object of this invention is to provide a positron-computed tomograph device incorporating a mechanism capable of holding the noise due to accidental coincidence to a low level even when the radioactive intensity of the emission source for attenuation correction is high, reconstructing an image with high resolvability, and exhibiting outstanding adaptability to various devices.

To accomplish the object described above according to the present invention, there is provided a positron-computed tomograph device which comprises a means for measuring the angle of rotation of the gamma ray source for attenuation correction revolved around the subject and a means for selectively memorizing only the coincidence measured by the particular pair of scintillation detectors placed in coincidence operation when the emission source is present on the coincidence line connecting the detectors.

By the measurement of the relative angle of rotation between the emission source and the pair of scintillation detectors, it can be determined whether or not the emission source is present on the coincidence line. The pair of scintillation detectors are made non-responsive or the coincidence data are prevented from being stored in the memory when the emission source is not present on the coincidence line. Consequently, it is possible to hold accidental coincidence and scattered coincidence at low levels.

The other objects and characteristic features of the present invention will become apparent to those skilled in the art as the further disclosure is made in the following description of the preferred embodiment illustrated in the accompanying drawings.

BRIEF DESCRIPTION OF THE DRAWINGS

FIG. 6 is a block circuit diagram according to another embodiment of the present invention.

DESCRIPTION OF THE PREFERRED EMBODIMENT

This invention relates to a positron-computed tomograph (PCT) device incorporating therein a mechanism for suppressing the noise component of the data for attenuation correction.

Figure 1:
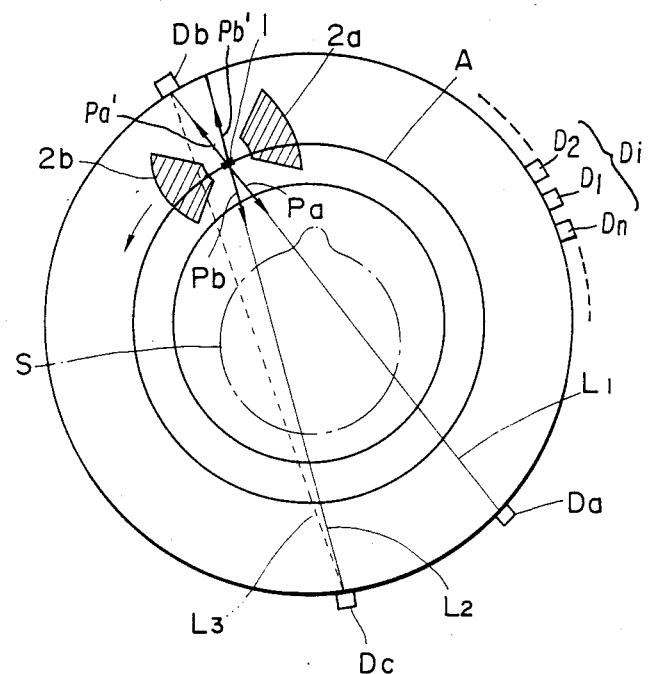
FIG. 1 is a schematic diagram illustrating a mechanism for suppressing noise during the attenuation correction in the conventional position CT device.

First, the mechanism heretofore contemplated for the suppressing of noise will be described with reference to FIG. 1. Here, lead shields $2a$, $2b$ are disposed one each at the opposite sides of a gamma ray source 1 for attenuation correction which is revolved along an orbit A in the space between the subject S and scintillation detectors $D_i$ (i=1, 2, ... n) circumferentially spaced around the subject S. These shields $2a$, $2b$ are effective in shielding from the radiation those scintillation detectors which fall outside the zones exposed to the gamma rays emitted through the apertures in the enclosure formed by the shields. It is now assumed that a pair of annihilation gamma rays are emitted from the source 1 in the direction of Pa and in the diametrically opposite direction Pa' and the annihilation gamma rays are caught coincidently on the respective scintillation detectors $D_a$, $D_b$. Then at the next moment, namely, a very brief time after the emission of annihilation gamma rays in the Pa and Pa' directions, one pair of annihilation gamma rays are subsequently emitted in the direction Pb and the diametrically opposite direction Pb' and one of these annihilation gamma rays is caught on the scintillation detector $D_c$. By reason of the performance of the coincidence circuit, the mechanism under discussion regards this phenomenon as though the annihilation gamma rays in the Pa direction and the Pb direction were simultaneously caught on the scintillation detectors $D_a$, $D_c$. Consequently, there are times when coincidence may be detected between the scintillation detector $D_b$ and the scintillation detector $D_c$ which falls within the zone of exposure to the source 1 (line $L_2$) and nevertheless is opposed to the scintillation detector $D_b$ (line $D_3$) within the aforementioned zone of exposure at the same time that the scintillation detectors $D_a$, $D_b$ are put in coincidence with each other on the coincidence line $L_1$. This is the very accidental coincidence that constitutes the noise component in a reconstructed image. Thus, the effort to eliminate the noise component from the data for attenuation correction by the use of such shields has its limit.

The inclusion of the noise in the measured data may be ascribable in one aspect to the following action of the conventional circuit for collection of data. A close look at the scintillation detector pair (all the detectors are connected in pairs via coincidence circuits) reveals that no matter what position the source for atteuation correction may assume on the orbit for the source, the coincidence circuits and the data collection circuit continue to operate and take in all the coincidence data detected. It is, however, only during the time when the source is present within the zone of coincidence of the scintillation detector pair that the scintillation detector pair detects true coincidence. Only such noise as accidental coincidence is detected at any other time.

Owing to its entirely novel concept, the present invention successfully suppresses the accidental coincidence and the scattered coincidence which inevitably occur in the measured data as described above and makes possible reconstruction of an image with high quality. The technical concept of this invention will be outlined below. This invention succeeds in keeping down accidental coincidence and scattered coincidence to low levels by employing a means capable of detecting the relative angle of rotation between the source and the relevant scintillation detector pair and consequently determining whether or not the source is present within the zone of measurement of the scintillation detector pair of interest and either a means capable of precluding the measurement of coincidence or a means capable of preventing the measured data of coincidence from being stored in memory in case where the source is not present in the relevant zone of measurement. Now, the invention will be described in detail below with reference to the accompanying drawings.

Figure 2:
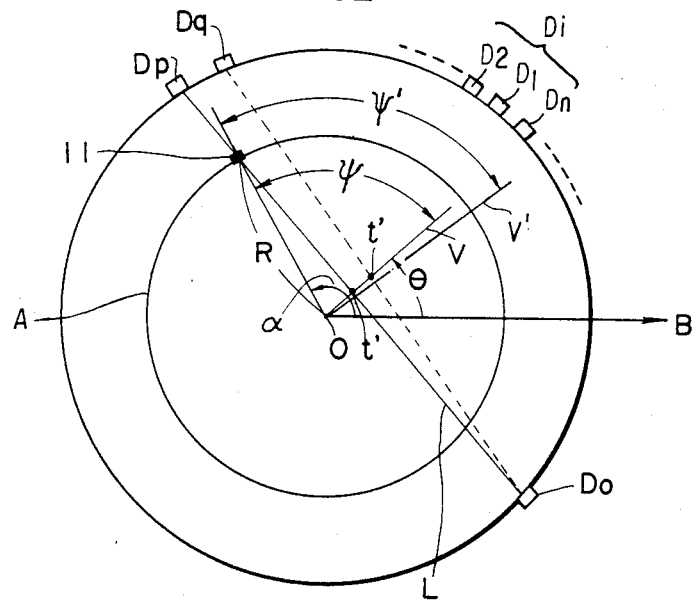
FIG. 2 is a schematic diagram illustrating a mechanism for suppressing noise during the attenuation correction in one embodiment of the positron CT device according to this invention.

FIG. 2 is a diagram illustrating the principle of this invention concerning the relative positions assumed by the scintillation detector pair and the gamma ray source 11 at the moment that the source 11 assumes its position on the coincidence line L between the scintillation detectors $D_o$, $D_p$. Here, let R stand for the radius of the orbit A traced by the source, V for the perpendicular line from the coordinate origin O to the coincidence line L, t for the space coordinates from the origin O to the point of intersection between the coincidence line L and the line V, $\theta$ for the angle contained between the line V and the base line B in the stationary system, and $\alpha$ for the angle between the source 11 and the base line B, and the following equations will be satisfied.

$$R \cdot \cos \psi = t \qquad (1)$$

$$\psi = \alpha - \theta \qquad (2)$$

where $\psi$ is an angle between the source 11 and the line V.

These equations disregard the width of the scintillation detectors and the expansion of the source.

The equations imply that the positions of the scintillation detector pair on any coincidence line relative to the position of the source 11 as viewed from the stationary system may be designated with the space coordinates t. When the source 11 and a given scintillation detector pair fall on one coincidence line, they will assume their specific values of space coordinates which are expressed by t. So, the values of space coordinates t of the points to be given by all the coincidence lines that can be formed with respect to the positional angle of the source 11 throughout the entire orbit A are calculated and stored in the memory in advance.

During the scanning for attenuation correction, the source revolved along the orbit A continues to emit gamma rays and the relevant scintillation detector pairs successively take count of coincidence and the memory keeps record of the measured data. After a proper interval, the data are read out of the memory to find the rotational angles $\alpha$ of the source assumed at the moments at which coincidence is detected and the angles $\theta$ derivable from the positions at which the relevant scintillation detector pair caught gamma rays at the moments of the occurrence of coincidence. Then, the values ($R \cdot \cos \psi$) are calculated based on values $\alpha$ and values $\theta$. The values ($R \cdot \cos \psi$) thus obtained and the values t computed in advance with respect to the position of the source and stored in the memory are collated to determine the moments at which values ($R \cdot \cos \psi$) and values t were approximately equal. The measured data obtained at these moments are separated out and stored as data of true coincidence. When coincidence is measured by the scintillation detector pair $D_o$-$D_p$ while the source is at the position indicated in FIG. 2, the value ($R \cdot \cos \psi$) obtained at this particular moment may be recognized as representing true coincidence if it is either identical with or approximately equal to the value t calculated in advance with respect to that particular moment. If the scintillation detector pair $D_o$-$D_q$ measures coincidence and the intersection point t' of the coincidence line (dotted line) on the line perpendicular line V', which is drawn from the origin O to the line Do-Dg and defined by the angle $\psi'$, is compared with the value t set and collated in advance and consequently is found to involve a difference exceeding the allowable limit, then the coincidence in this case may be recognized as representing accidental coincidence. By preventing values of such accidental coincidence from being included in the measured data, therefore, the desired elimination of the noise component from the data is accomplished in effect. Of course, elimination of values of scattered coincidence can be attained similarly.

The scanning system of FIG. 2 is of a ring type non-scanning mode making use of a ring of stationary scintillation detectors. Theoretically, the present invention can be applied by the same principle to any of the aforementioned devices, namely, the device utilizing a wobbling scanner, the device of straight-rotary composite scanning, and the device of dichotomic scanning. As another embodiment of this invention, a positron-CT device of the continuous rotary scanning mode which has a ring of detectors unevenly disposed and, therefore, causes the source and the detectors to effect rotary scanning at dissimilar speeds will be described with reference to FIG. 3. For information on the continuous rotary scanning mode, see "N. Nohara, et al. 'POSITOLOGICA: A Positron ECT Device with a Continuously Rotating Detector Ring,' IEEE Trans. Nucl. Sci., NS-27, No. 3, pp. 1128–1136".

This CT device is provided with a collimator 12 which comprises two annular lead shields 12a, 12b opposed to each other across a circumferential space 13 serving as a path for gamma rays. One of the shielding members, 12b, of the collimator 12 is divided into an inner ring and an outer ring spaced by a uniform annular gap 14. These inner and outer rings are adapted to be rotated about a shaft 15 and are fastened to a detector support 21 having a plurality of detectors 20 stationarily carried thereon. A cylindrical source support 16 is rotatably disposed within the annular gap 14 intervening between the opposed peripheries of the inner and outer rings of the shielding member 12b of the collimator 12. A gamma ray source 11 is retained at the leading end of the source support 16.

The source 11 retained at the leading end of the source support 16 is adapted so as to be accommodated within the annular gap 14 formed in the shielding member 12b of the collimator 12 by suitable means. Only when the gamma ray source 11 is put to use for the purpose of attenuation correction, is it protruded into the path 13 for gamma rays. When it is out of use, it is kept retracted in the annular gap 14.

The rear end of the source support 16 is connected through a gear mechanism 17 to a drive shaft 18. By rotating the drive shaft 18, therefore, the source support 16 is rotated relative to the detector support 21. Thus, the source 11 and the detectors $D_i$ ($i = 1, 2, \ldots n$) produce a rotary motion relative to each other.

The relative rotary motion between the emission source 11 and the standard detector $D_s$ ($s = 1$) is detected by the cooperation of a zebra scale 19a and a zebra scale sensor 19b provided respectively on the detector support 21 and the source support 16. The zebra scale 19a on the source support 16 side has the shape of a tube and has parallelly disposed on the inner surface of this tube a plurality of circumferential stripes each having alternating reflection and non-reflection bands arranged at dissimilar pitches relative to those of the other stripes. The number of these stripes may be suitably selected, depending on the angular resolvability desired to be attained. in the present embodiment, the zebra scale 19a has eight such stripes and, therefore, is capable of obtaining 8-bit angle data. The zebra scale sensor 19b comprises a light source and a light receiving element opposed to each other. It is disposed on the detector support 21 so that it will confront the aforementioned zebra scale 19a disposed on the source support 16 when the source 11 is protruded into the path 13 for gamma rays for the purpose of attenuation correction. For the measurement of the displacement in the relative angle, the light from the light source of the zebra scale sensor 19b is projected on the stripes of the zebra scale 19a and the light reflected by the zebra scale 19a and carrying thereon the information as to the bright and dark bands of the zebra scale 19a is admitted into the light receiving element of the zebra scale sensor 19b. In the present embodiment, there are consequently obtained data in the form of 8-bit digital signals. These digital signals permit determination of the relative angle between the source 11 and the standard detector $D_s$. Optionally, the relative angle $\beta$ between the source 11 and the standard detector $D_s$ may be determined by the use of a suitable angle detecting device such as an angle encoder.

The plurality of detectors $D_i$ parallelly disposed on the periphery of the collimator 12 comprise scintillators 20a and photomultiplier tubes 20b disposed around the outer opening of the path 13 for gamma ray in the collimator 12. These detectors $D_i$ are provided with coincidence circuits which fed out data whenever it detects coincidence.

The rotary shaft 15 of the detector support 21 is provided at one end thereof with an angle encoder 22 adapted to read out the rotational angle of the detector support 21 having the detectors $D_i$ and the collimator 12 secured thereon.

This rotary shaft 15 is further provided with a rotary photocoupler 23 adapted to transfer from the rotary system to the stationary system the address signal designating the detector pair which has detected coincidence when the coincidence is detected by the coincidence circuit. One possible configuration of this rotary photocoupler 23 has been proposed by Japanese Patent Publication No. Sho 55(1980)-90145, for example. These photocouplers comprise a plurality of light-emitting diodes (LED) disposed on the rotary system side and a plurality of photodiodes (PD) disposed on the stationary system side. The number of these LED's equals the number of data bits to be transferred. In the present embodiment, this is the total of the bits required for representing the address designating the detector pairs which have detected coincidence and the angle data regarding the relative angle between the source and the standard detector and received from the zebra scale, the flag bit (one bit) for the delayed coincidence required in calculating true coincidence by the subtraction of accidental coincidence from prompt coincidence as will be touched upon afterward, etc. The present embodiment makes use of a total of 24 bits, i.e. 12 bits for designating the address of the detector pair, 8 bits for the angle data and the rest 4 bits including 1 bit for the delayed coincidence. Thus, the number of LED's used in the present embodiment is 24. These LED's are placed at twenty-four of 32' equally divided positions on the same radius of gyration on a disc-like member provided on the rotary shaft 15.

The photodiodes disposed on the stationary system so as to confront the LED's disposed on the rotary system function to receive the bit signals emitted from the LED's which revolve and emit light at extremely short time intervals. To ensure safe reception of these bit signals by the PD's, it is desired to use PD's in a number more than twice the number of LED's (generally, PD's of $2^n$). In the case of the present embodiment, a total of 64 PD's are disposed. In this case, it suffices to dispose switch circuits on the PD output side so that either row of PD's which are opposed to the LED's are allowed to assume an operating state at any given moment in accordance with the data on the rotational angle given by the aforementioned angle encoder 22. To read out accurately the sequence of the plurality of bits transferred parallelly from the LED's in rotation, these bits are processed on the basis of the data of the rotational angle from the angle encoder 22.

Basically by the configuration described above, the present embodiment is enabled to determine the relative angle between the source 11 and the detector ring composed of the detectors $D_i$ rotated at dissimilar speeds and their respective absolute angles relative to the stationary system.

In one working example, the speeds of rotation of the source and the detector ring were as shown below. The width of the emission source was fixed at 7.6 mm, which is 1/128 of the length of the orbit of the source. The source was revolved along the orbit at a speed of 7/128 of the speed of rotation of the detector support 21. When the detector ring makes 128 rotations, therefore, the source completes seven revolutions and finishes measurement for obtaining data for attenuation correction. Since the detector ring approximately completes one rotation per second, the complete measurement takes about 128 seconds. One mechanism required in setting the speed of rotation at this particular proportion has already been proposed by Japanese Unexamined Patent Application Disclosure No. Sho 55(1980)-129780. It constitutes none of the essential elements for the construction of this invention. Thus, the mechanism is not described any further here.

Figure 4:
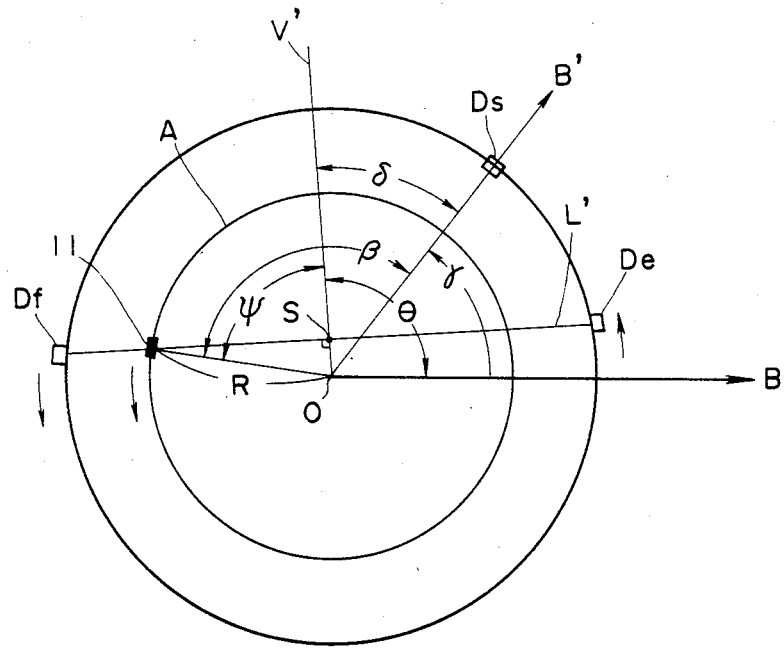
FIG. 4 is a schematic diagram illustrating a mechanism for suppressing noise during the attenuation correction in another embodiment of the positron CT device according to the present invention.

In the configuration in which the source and the detector ring are moved at dissimilar speeds as described above, detection of coincidence by a specific detector pair and identification of this particular coincidence to be either true coincidence or accidental coincidence are obtained by generation of the same state as illustrated in FIG. 2, namely, by determination of the positions of the detector pair which have detected coincidence and the position of the source. A method for determining such angular positions will be described below with reference to FIG. 4.

It is now assumed that the detector pair $D_e$-$D_f$ have detected coincidence when the detector support 21 reaches its standard position relative to the base line B in the stationary system or when a specific detector is rotated by an angle $\gamma$ and brought to the standard line B'. The aforementioned angle $\gamma$ is constantly monitored by the angle encoder 22. The positions of the detector pairs $D_e$-$D_f$ which have detected coincidence relative to the standard line B' are found from the address signal issued when the coincidence data are read out. Consequently, the coincidence line L' as viewed from the stationary system side can be found at the same time. This line L' may be stored in advance in the memory as the function of all conceivable positions of the detector pair. Similarly, the perpendicular line V' drawn from the origin O of the rotaty system to the line L' and the angle $\delta$ formed between the standard line B' of the detector support and the aforementioned perpendicular line V' may be stored in advance in the memory as functions of the positions of the detector pair which detect coincidence so that they will be readily read out when needed. Then, the angle $\psi$ between the source 11 and the perpendicular line V' is calculated in accordance with the following formula:

$$\psi = \beta - \delta \tag{3}$$

Then, the value ($\cos \psi$) is read out of the memory and the distance coordinates of the intersection point, s, between the line L' and the perpendicular line V' is calculated in accordance with the following formula:

$$S = R \cdot \cos \psi \tag{4}$$

Further, by the addition of $\gamma$ and $\delta$, the angle $\theta$ formed between the base line B and the perpendicular line V' (which equals $\theta$ in the diagram of FIG. 2) is calculated as follows:

$$\theta = \gamma + \delta \tag{5}$$

The value s found as described above is now compared with the distance coordinates t at which the imaginary line connecting one of the detector pair, $D_e$, and the source 11 intersects the perpendicular line V' (the distance coordinates stored in the memory in advance as functions of the position of the source 11 and all the detectors $D_i$ as described above). If the absolute value of the difference between s and t is smaller than the constant c which will be described afterward, then the coincidence detected by the detector pair $D_e$-$D_f$, are recognized as the data representing (prompt) coincidence. Thereafter, the image of the desired plane section is obtained by following the ordinary procedure of image reconstruction. This procedure is well known and does not require any particular mention here. By this method, a level of accidental coincidence high enough to conspicuously affect the reconstructed image finally produced is effectively prevented. As concerns the low level of accidental coincidence which is still contained in the prompt coincidence, when the coincidence data obtained by the aforementioned method are stored in the region of the memory table designated by the addresses (t, $\theta$), one count is added to the entry in the specific region of the memory table mentioned above upon the detection of the prompt coincidence, or one count is subtracted from the resultant signal to be stored in the specific region of the memory table upon detection of the delayed coincidence. Consequently, the deviation due to the accidental coincidence can be corrected. The fact that the formula (3) and the formula (2) are equivalent is evident from the formula (5) and the following formula.

$$\alpha = \beta + \gamma \qquad (6)$$

Now, the constant c will be described below. If the efficiency of true coincidence by a given detector pair relative to a given position of the source decreases, the intensity of the source fails to remain constant irrespective of the particular detector pair which detects coincidence. In this case, accurate attenuation correction cannot be obtained unless the intensity of the source is corrected by some means. Consequently, the accuracy of the sensitivity compensation of the detectors is impaired and the possibility of producing an artifact arises. Thus, the constant c should not be 0. Instead, in due consideration of the width of the detector and the width of the source, it must be fixed at a value which is incapable of lowering the rate of true coincidence. For this purpose, it suffices to define the angles such as $\alpha$, $\beta$ relative to the center of the source and fix the value c at the sum of one half of the width of the detector and one half of the width of the source. In the aforementioned working example, the constant c is fixed at 10 mm (width of 5 bins) because t is digitized with 128 channels using 2 mm of bin width so as to give 256 mm of field of view, and the width of the detector is 12 mm and the width of the source is 7.6 mm. For a given value of the angle $\theta$, coincidence data are taken in only with respect to the value of each set of eleven t's. Consequently, it is during 11/128 of the total time of counting that the coincidence data are injected from the relevant detector pair into the memory. Thus, the frequency of accidental coincidence included in the measured data is notably decreased.

The embodiment described above treats the value c as a constant. When the positional resolvability of the detector (equivalent to the width of the detector) is appreciably varied with the value t, however, the value c is desired to be fixed as a function of t.

Figure 3:
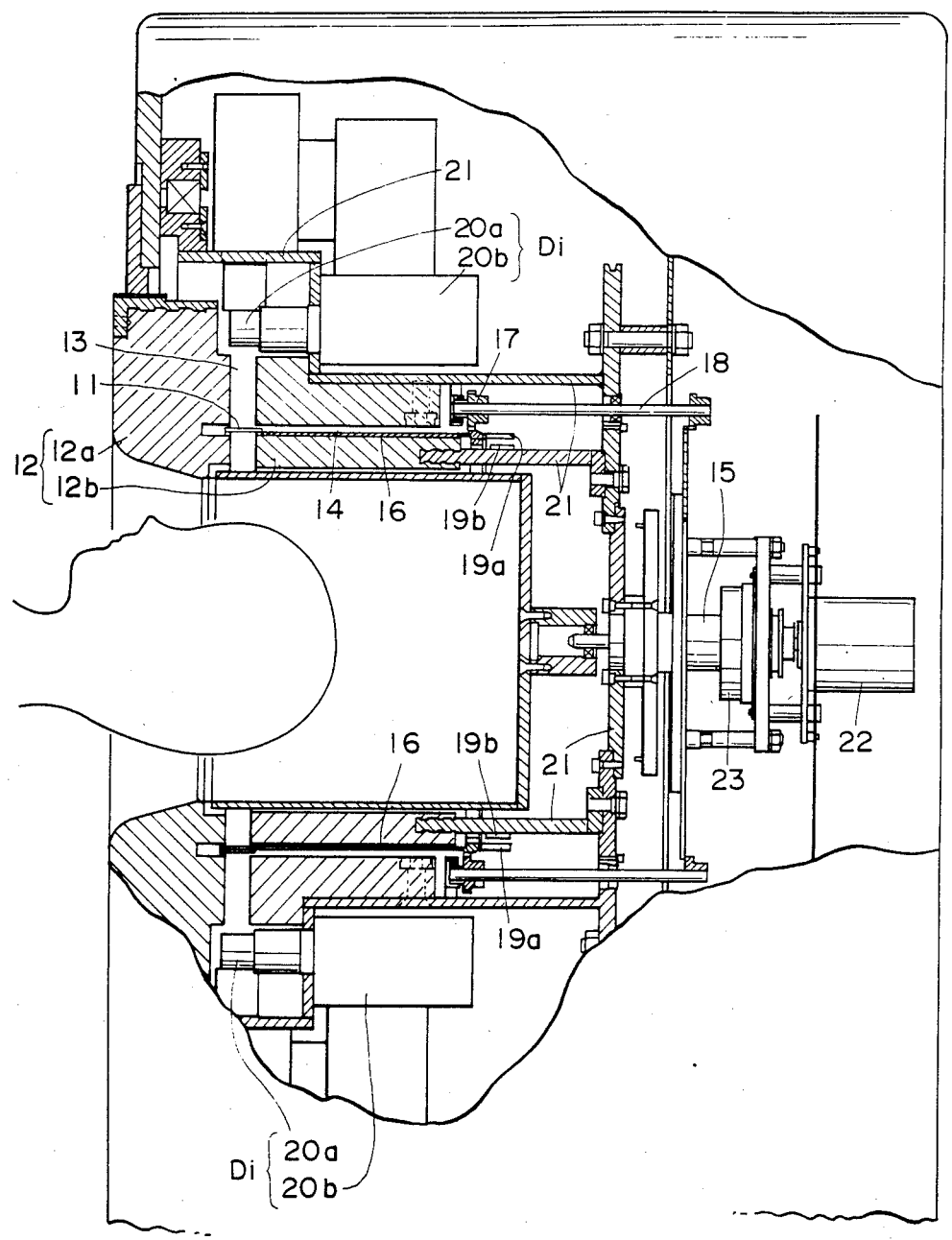
FIG. 3 is a sectioned side view illustrating the essential part of one embodiment of the positron CT device according to the present invention.
Figure 5A:
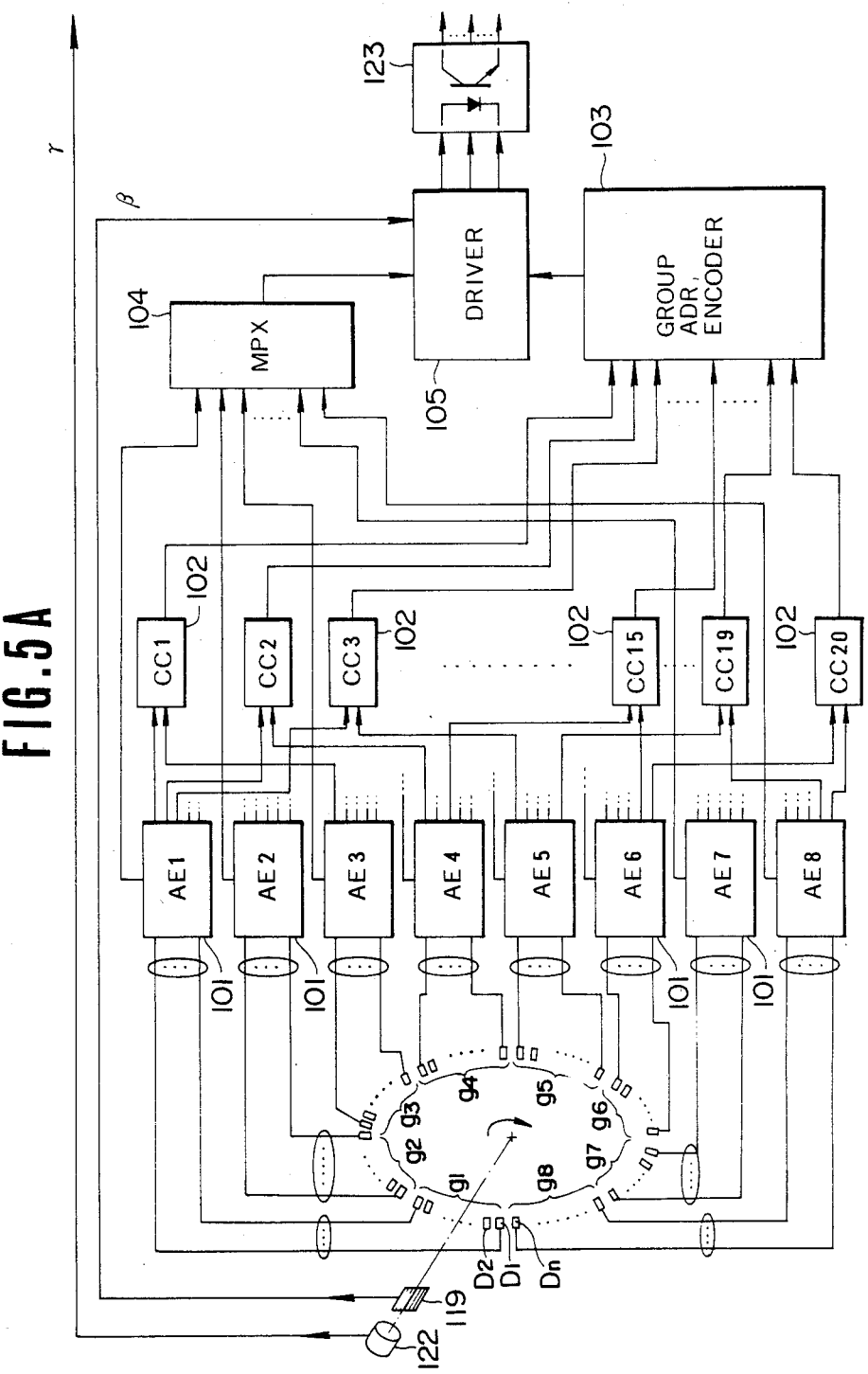
FIGS. 5A and 5B are schematic circuit diagrams according to one embodiment of this invention.
Figure 5B:
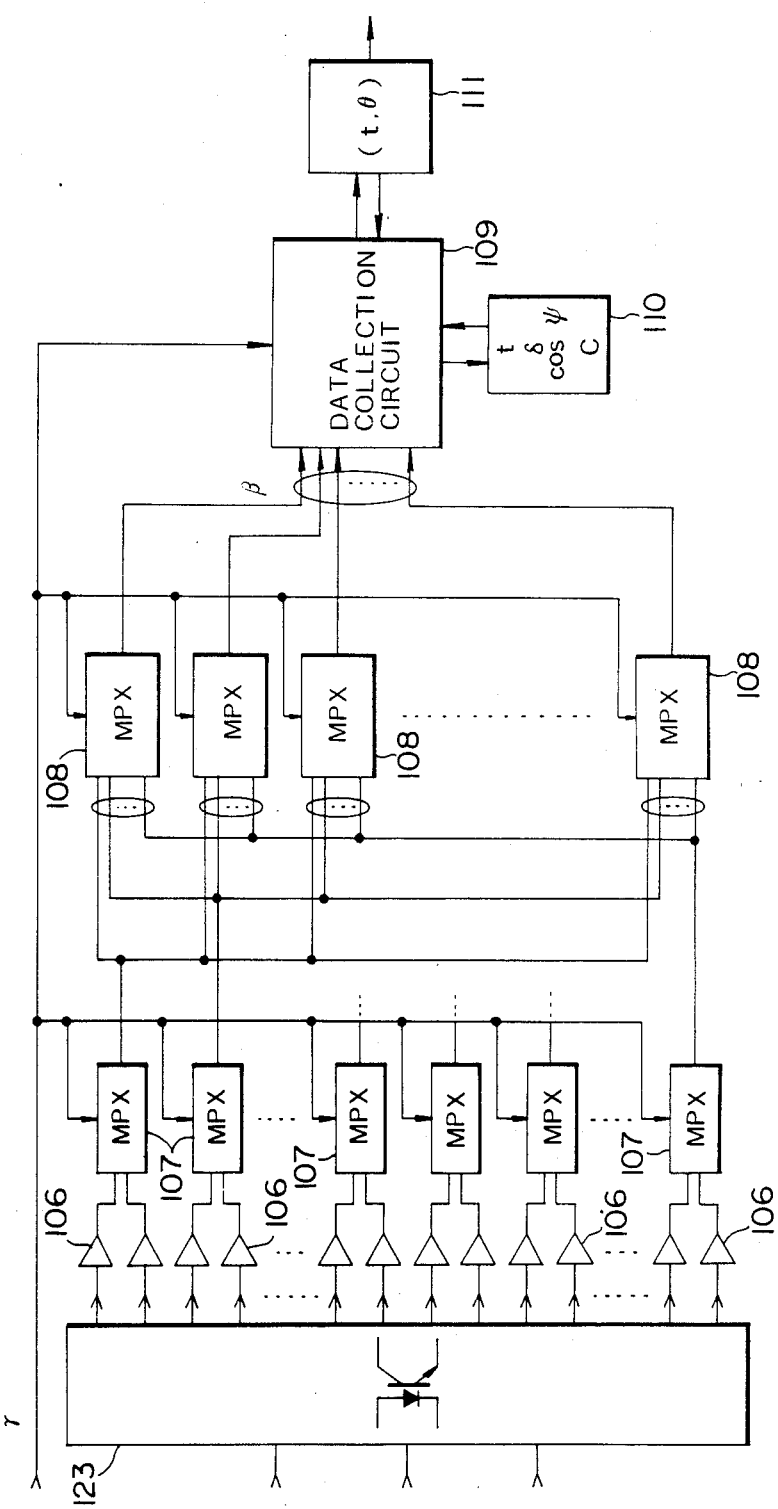

The configuration of circuits in the CT device of this invention will be outlined with reference to FIGS. 5A and 5B as compared with the configuration of FIG. 3. Roughly, FIGS. 5A and 5B may be distinguished as respectively depicting the rotary system and the stationary system of this invention.

Referring now to FIG. 5A, the ring of detectors $D_1$, $D_2$, ... $D_n$ (n=64 is assumed herein) which are circumferentially arranged are divided into a plurality of groups (whose number is represented by Ng). In the present embodiment, there are 8 groups $g_1$-$g_8$ each composed of 8 detectors. The individual groups each retain a non-responsive state relative to their immediately adjacent groups. Thus each group is validated to detect coincidence with the five groups (Na) opposed thereto.

Each of the detectors $D_i$ ($1 \leq i \leq n$) is connected to the address encoder 101 ($AE_1$-$AE_8$) which is allocated to the relevant group. Consequently, the timing signals from the detectors are fed to the corresponding address encoders 101, the addresses of the eight detectors in each group are binary-coded, and the timing signals are fed to the coincidence circuits 102 ($CC_1$-$CC_{20}$), depending on the conditions under which the individual detector group are opposed to the respective five detector groups. The number Nc of coincidence circuits 102 can be expressed at Nc=Ng×Na/2, when Ng=8 and Na=5 in the aforementioned arrangement of the detectors, the number of detector pairs for coincidence becomes 20. The outputs of the coincidence circuits 102 are delivered to the group address encoder 103 to seek out the particular address encoder 101 involved in the detection of coincidence. As the other output from the address encoder 101, the addresses within the relevant group are multiplexed by a multiplexer 104 and then fed out. The outputs respectively of the group address encoder 103, the multiplexer 104, and the zebra scale sensor 119 drive the light-emitting element of the photocoupler 123 of the aforementioned construction via the LED driver 105 and are then transferred to the light-receiving side.

FIG. 5B illustrates the stationary system having as its input terminals the light-receiving element such as photodiodes of the photocoupler 123. The number of bits by which the input to the photocoupler 123 is conveyed is in due proportion to the size of the address of the detector and the angular data received from the zebra scale sensor 119. In the case of the present embodiment, 24 output signals are obtained from the total of 48 PD's, i.e. the sum of 12×2 PD's for the address of the detectors, 8×2 PD's for the angle data, and the rest 4×2 PD's including 1×2 PD's for delayed coincidence. The outputs are amplified by an amplifier 106. Since 2 PD's are used for each LED as already described, the amplified outputs are sent to multiplexers (MPX) 107 along with the signals on angle from the angle encoder 122 through circuits such as Schmitt trigger circuits (not shown) to obtain outputs corresponding to the LED's of the photocouplers 23. These outputs are further fed to respective multiplexers 108 along with the signals on angle from the angle encoder 122 so that those for the address of detector and those for the angular data from the zebra scale sensor may be multiplexed separately of each other. The outputs of the multiplexers are fed to the data collection circuit 109 together with the signals on angle from the angle encoder 122. The data collection circuit 109 takes in all the data obtained, reads out the coefficients and constants such as t, $\delta$, cos $\psi$, L', V', and c which have been stored in advance in the memory 110, and performs the calculations of the formulas (3)-(5). The data containing the addresses (t, $\theta$) obtained as described above are accumulated in the designated regions of the matrix table of the memory 111. Of course, in this case, the values of the aforementioned delayed coincidence are duly subjected to addition or subtraction.

The data thus obtained are smoothened and used for attenuation correction of the data for image reconstruction by the ordinary method.

In contrast to the preceding embodiment which relies on the stationary system to effect the required selection of coincidence from the specific detector pair, another embodiment whose basic concept is depicted in FIG. 6 is designed to effect this selection in the rotary system. The configuration of circuits in the present embodiment is not conspicuously different and the operating principle is similar.

Now, the embodiment will be described below with reference to FIG. 6. While the coincidences obtained by the detectors Di are detected by the coincidence circuit 202, the output $\beta$ from the zebra scale sensor 219 is constantly fed to the coincidence selector 220 provided on the detector support. The coincidence selector 220 reads $\delta$ out of the memory provided on the detector support to calculate $\psi$ and reads $(\cos \psi)$ out of the memory 210 to calculate s therein. It further reads t out of the memory 210 and feeds out the data on t and $\delta$ only when the absolute value of the difference between t and s is found therein to be less than c. The data are transmitted through the rotary photocoupler 223 to the data collecting circuit 212 on the stationary side. The data collection circuit 212 computes $\theta$ on a basis of the output $\gamma$ of the angle encoder 222 and the values $\delta$ transmitted via the rotary photocoupler 223 and makes addition or subtraction of one count to or from the region designated by the address (t, $\theta$) within the memory 211. Owing to the configuration of circuits described above, the present embodiment is enabled to decrease notably the rate of accidental coincidence passing the rotary photocoupler and elevate the property of obstructing mis-counting so as to retain high counting ratio in the entire system.

The embodiments so far described have assumed the system to be operated by the use of one gamma ray source. Of course, the positron CT device of this invention may be operated by the use of a plurality of gamma ray sources. In this case, the values s and the absolute values of differences between t and s are subjected to computation for every source. The data may be stored in the memory as measured data when at least one of the absolute values of the aforementioned differences is less than the value c.

The foregoing embodiments have been described with respect to positron CT devices of the type having the ring of detectors and the source invariably rotated continuously. The present invention has absolutely no need to limit the mode of scanning to rotary motion. It can be applied to any method by which the source is enabled to effect required scanning of the subject. Even when the mode of scanning is varied, the equations (1) and (2) are satisfied. Of course, the present invention is applicable insofar as the values of $\alpha$ and $\theta$ are obtainable from the equation (2).

This invention, of course, is applicable not only to the attenuation correction involved in the collection of data on transmittance through a subject but also to the collection of data on sensitivity compensation by the operation of the positron CT device in the absence of a subject in the field of view. The embodiments described in detail above have assumed adoption of devices provided with built-in sources. From the embodiments, it should be clear to those skilled in the art that this invention is applicable to positron CT devices of the type adapted to permit spot attachment of sources preparatory to collection of data for attenuation correction or data for sensitivity compensation.

Moreover, this invention is applicable to any of the various devices such as the device utilizing a wobbling scanner, the device involving straight-rotary composition scanning, the device involving dichotomic scanning, and the non-scanning device.

It is further clear to those skilled in the art that this invention, in addition to being applicable to the positron CT device of single-layer scanning, is applicable in its unaltered form to the positron CT device adapted to collect data on multiple layers.

As described above, the present invention provides notable suppression of the noise component of the data for attenuation correction. When the intensity of the source for attenuation correction is increased to several times the conventional level, therefore, the data for attenuation correction can be obtained in a very short length of time and the statistical noise entrained by the data can be decreased to a great extent. Thus, the image of the plane section to be finally obtained by this invention enjoys high quality and entrains no noticeable statistical noise.

What is claimed is:

1. A positron-computed tomograph device in which attenuation correction in image reconstruction is effected by revolving a gamma ray source around a subject and scanning said subject with gamma rays emitted from said gamma ray source and causing a certain opposed detector pair out of a plurality of circumferentially spaced detectors to detect coincidence, which device comprises:

a means for measuring the relative positions of said opposed detector pair with respect to said source at the time of detection of said coincidence and computing data on the relative positions thus measured;

an arithmetic circuit for allowing the values of said data on the relative position of said opposed detector pair with respect to said source at the time of detection of said coincidence to be compared with predetermined values of data on the position of all possible opposed detector pairs relative to all possible positions of said source and determining whether or not the differences between said values of data obtained at the time of detection of said coincidence and said predetermined values of data fall within a certain allowable range; and a memory for storing said data on the positions of said opposed detector pair relative to the position of said source when said comparison effected in said circuit has ascertained that said differences between said values obtained at the time of detection of said coincidence and said predetermined values of data fall within said allowable range.

2. A positron-computed tomograph device according to claim 1, wherein said plurality of detectors are set in position on a stationary system and said means for measuring the relative positions incorporates therein an angle encoder which measures the angle representing the relative position of said source with respect to a standard detector of said plurality of detectors while revolving around the subject said source to effect the scanning.

3. A positron-computed tomograph device according to claim 1, wherein said group of detectors and said emission source are allowed to be revolved at different speeds around said subject to effect the scanning and said means for computing data on the relative positions incorporates therein an angle encoder set fast in position on a stationary system and adapted to measure the angle representing the position of a standard detector of said plurality of detectors and an angle detection means for measuring the relative angle between said standard detector and said source.

4. A positron-computed tomograph device according to claim 3, wherein said angle detection means for measuring the relative angle between said standard detector and said source is a zebra scale sensor.

5. A positron-computed tomograph device according to claim 3, wherein said means for measuring the relative positions incorporates therein coincidence circuits for taking coincidence out of the output signals obtained by said plurality of detectors and address encoders for designating the addresses of said specific opposed detector pair which has detected said coincidence and said arithmetic circuit incorporates therein a data collection circuit for admitting data on the relative positions obtained in consequence of address designation in said means for measuring the relative positions.

6. A positron-computed tomograph device according to claim 5, wherein said coincidence circuit and said address encoder are provided in a rotary system and said data collection circuit is provided in a stationary system respectively and said rotary system and said stationary system are connected with a photocoupler adapted to transfer data between said two systems.

7. A positron-computed tomograph device according to claim 3, wherein said coincidence circuit for taking coincidence out of the output signals obtained by said plurality of detectors, said address encoder for designating the addresses of said specific opposed detector pair which have detected said coincidence, and said coincidence selection circuit for comparing the data on the relative positions obtained in consequence of said address designation with predetermined values of data are provided in a rotary system, said data collection circuit for compiling and storing in a memory the data resulting from comparison of data on relative positions obtained in consequence of said address designation with predetermined values of data is provided in a stationary system, and said rotary system and said stationary system are connected with a photocoupler adapted to transfer data between said two systems.

* * * * *